United States Patent [19]
Conrad

[11] Patent Number: 6,054,299
[45] Date of Patent: Apr. 25, 2000

[54] STEM-LOOP CLONING VECTOR AND METHOD

[76] Inventor: Charles A. Conrad, 5807 Miller Valley, Houston, Tex. 77066

[21] Appl. No.: 08/877,251

[22] Filed: Jun. 17, 1997

Related U.S. Application Data

[63] Continuation of application No. 08/236,504, Apr. 29, 1994, abandoned.

[51] Int. Cl.$^7$ .................................................... C12N 15/00
[52] U.S. Cl. .................... 435/91.1; 435/91.4; 435/320.1; 435/252.3
[58] Field of Search .............................. 435/172.3, 320.1, 435/91.1, 252.3

[56] References Cited

PUBLICATIONS

Beggs, Nature 275: 104 (1978).
Colvin, Richard A., et al., "Strucural Features of an RNA Containing the CUGGGA Loop of the Human Immunodeficiency Virus Type 1 Trans–Activation Response Element," Biochemistry 1993, 32, 1105–1112.
Pollack, Jonathan R., et al., An RNA Stem–Loop Structure Directs Hepatitis B. Virus Genomic RNA Encapsidation, Journal of Virology 3254–3263 (Jun. 1993).
D'Souza, D.J., et al. "Strong Binding of Single–stranded DNA by Stem–Loop Oligonucleotides," Journal of Biomolecular Structure & Dynamics 10:141 (1992).
Ohshima, A., et al. "In vivo duplication of genetic elements by the formation of stem–loop DNA without a RNA intermediate," Biochemistry 89:1016 (1992).
Mead, D.A., et al. "A universal method for the direct cloning of PCR amplified nucleic acid," Biotechnology, vol. 9:657 (1991).
Xodo, L.E., et al. DNA hairpin loops in solution. Correlation between primary structure, thermostability and reactivity with single–strand–specific nuclease from mung bean, Nucleic Acides Research 19:1505 (1991).
Barabino, Silvia, et al., "Antisense probes targeted to an internal domain in U2 snRNP specifically inhibit the second step of pre–nRMA splicing," Nucleic Acids Research, vol 20, No. 17, 4457–4464 (1992).
Nag, Dilip K., et al. "Seven–Base–Pair Inverted Repeats in DNA Form Stable Hairpins in Vivo in Saccharomyces cerevisiae,"Genetics 129: 669–673 (Nov. 1991).
Vickers, T., et al. "Inhibition of HIV–LTR gene expression by oligonucleotides targeted to the TAR element," Nucleic Acids Research, vol. 19, No. 12, 3359–3368 (1991).
Vieira, J., et al. Production of single–stranded plasmid DNA, Methods Enzymol 153:3 (1987).
Baumann, U., et al. "Conformational analysis of hairpin oligodeoxyribonucleotides by a single–strand–specific nuclease," Eur. J. Biochem. 161:409 (1986).
Peeters, B.P.H., et al. Plasmid pKUN9, a versatile ector for the selective packaging of both DNA strands into single–stranded DNA–containing phage–like particles, Gene 41:39 (1986).
Yanisch–Perron, C., "Improved M13 phage cloning vectors and host strains: Nucleotide sequences of the M13mp18 and pUC19 vectors," Gene 33:103 (1985).
Levinson, A., et al. "Minimal size plasmids containing and M13 origin for production of single–strand transducing particles," J. Mol. Appl. Genet. 2:507 (1984).
Drew, Horace R., "Structural Specificities of Five Commonly Used DNA Nucleases," J. Mol. Biol. 176, 535–557 (1984).
Dente, L., et al. pEMBL: A new family of single stranded plasmids, Nucleic Acids Res. 11:1645 (1983).
Messing, J., et al. A new pair of M13 vectors for selecting either DNA strand of double–digest restriction fragments, Gene 19:269 (1982).
Beck, E., et al. "Nucleotide sequence and genome organization of filamentous bacteriophages f1 and fd," Gene 16:35 (1981).
Dotto, Gian P., et al., "Functional Analysis of Bacteriophage f1 Intergenic Region," Virology 114, 463–473 (1981).
Cleary, J.M., et al. Replication of the plasmid pBR322 under the control of a cloned replication origin from the single–stranded DNA phage M13, Proc. Natl. Acad. Sci. 77:4638 (1980).
Herrmann, R., et al. "Conversion of bacteriophage fd into an efficient single–stranded DNA vector system," Mol. Gen. Genet. 177:231 (1980).
Messing, J., "A multipurpose cloning system based on single–stranded DNA bacteriophage M13," Recomb, DNA Tech. Bull. 2(2):43 (1979).

(List continued on next page.)

*Primary Examiner*—James Martinell
*Attorney, Agent, or Firm*—Mark R. Wisner

[57] ABSTRACT

Methods and compositions for the isolation and specific targeting of any single stranded DNA sequence to be acted upon by any desired double stranded DNA genetic element or recognition sequence in a cis-oriented fashion. The invention involves construction of a vector comprised of single stranded sequences that form "stem-loop" structures wherein the "loop" comprises the single stranded target sequence and the "stem" comprises the double stranded "functional" cis-acting genetic elements or recognition sequences. The in vivo formation of this single stranded intermediate (prior to stem-loop folding) is performed by genetic elements which direct the normal DNA replication of any one of a number of prokaryotic and eukaryotic viruses during their life cycles. Constructs containing these replicative functions are used to produce the desired single stranded intermediates. Also included in the stem-loop structure is an appropriate inverted tandem repeat which, forms the "stem" of the stem-loop structure. Once these functions are designed into a particular chimera, any desired functional genetic elements (i.e., promoters, enhancer elements, or ribosome binding sites) or recognition sequences (i.e. restriction endonuclease sites) may comprise the inverted repeats and thus the cis-acting double stranded "stem" directs these useful functions to the isolated single stranded target sequence in the "loop".

18 Claims, 5 Drawing Sheets

OTHER PUBLICATIONS

Beck, E., et al. "Nucleotide sequence of bacteriophage fd DNA," Nucleic Acids Res. 5:4495 (1978).

Konings, R.N.H., et al. "Transcription of the filamentous phage genome," The Single–stranded DNA phages (ed. D.T.Denhardt et al.), 507 (1978).

Messing, J., et al. "Filamentous coliphage M13 as a cloning vehicle: Insertion of a HindII fragment of the lac regulatory region in M13 replicative form in vitro," Proc. Natl. Acad. Sci., 74:3642 (1977).

Marvin, D.A., Filamentous bacterial viruses, Bacteriol. Rev. 33:172 (1969).

```
          Bam III  Sac I    Not I    Hind III            Hind III  Not I    EcoR I   Xba I    Sac II
5'- CCG  GAT CCG  AGC TCG  CGG CCG  CCA AGC TT           A GCT TGG  CGG CCG  CGA ATT  CGC TCG  AGC CGC  GGG CTG 3'
3'- GGC  CTA CCG  TCG AGC  GCC GGC  GGT TCG A            TT CGA ACC  GCC GGC  GCT TAA  GCG AGC  TCG GCG  CCC GAC-5'
                                    (Inverted Repeat)    (Inverted Repeat)
```

Fig. 2A

```
C TCGCGGCCGCCAAGCTT-N- N
A AGCGCCGGCGGTTCGAA-N-
```

Fig. 2B

5'———— Not I  Hind III ———————————— Hind III  Not I ————3'
       Inverted Repeat    PCR Insert Piece    Inverted Repeat

Fig. 2C

STEM-LOOP CLONING VECTOR AND METHOD

This application is a continuation of application Ser. No. 08/236,504, filed on Apr. 29, 1994 now abandoned.

BACKGROUND OF THE INVENTION

The present invention relates to a stable DNA construct into which a target nucleic acid strand is incorporated for subsequent expression in a host. The construct includes inverted tandem repeats which form the stem of a stem-loop structure and which include one or more functional genetic elements having their function directed in cis-oriented fashion towards the single stranded target sequence.

Several researchers have created multi-functional, single stranded cloning vectors and cloning vectors which impart both single and double stranded DNA life cycle intermediates (i.e. phagmids). Additionally, naturally occurring stem-loop DNA and RNA structures are seen during the replicative cycle of viruses (predominantly) and cells and may have functional roles in DNA/RNA signaling mechanisms. Stem-loop structures have also been artificially produced primarily for DNA and RNA stability studies. However, so far as is known, there are no prior reports of the incorporation of genetic design into cloning vectors which allows for the stable formation of stem-loop structures (after conversion to single stranded intermediates) to perform useful functions to a target sequence(s) of interest that is located in the loop of the stem-loop structure by an isolated, functional, cis-acting double stranded genetic element (the stem).

The ability to form a stem-loop structure, after life cycle mediated single stranded conversion wherein the target sequence of choice (e.g., a cloned DNA fragment) is isolated as the so-called "loop" and is flanked by "functional" double stranded genetic elements (which form the so-called "stem") which direct the activities in cis-oriented fashion offers many advantages in performing useful manipulations to these target sequences. This structure, for instance, enables production of single stranded DNA probes which do not include the DNA sequences of the vector, thereby increasing their specificity over those made by known methods. Similarly, retroviral intermediates are constructed for drug delivery by triplex forming oligonucleotide production in vivo.

SUMMARY OF THE INVENTION

This advantage, and others which will be apparent to those skilled in the art who have the benefit of this disclosure, is provided by a cloning vector comprising a target nucleic acid sequence, a nucleic acid sequence which is a replicon, and a nucleic acid sequence which is an inverted tandem repeat flanking said target sequence and which includes a functional genetic element, said inverted tandem repeat forming a stable secondary structure stem-loop with said target sequence being located in the loop thereof. In a second aspect, the present invention contemplates a method of directing the expression of a single stranded nucleic acid sequence which comprises the steps of cloning a target sequence into a nucleic acid sequence and then forming the nucleic acid sequence having the target sequence cloned therein into a stem-loop structure by Watson-Crick base pairing of the nucleic acids comprising the nucleic acid sequence, the nucleic acids comprising the nucleic acid sequence having been selected so that when the nucleic acids thereof pair to form the stem-loop structure, the stem includes a functional genetic element having the function thereof directed towards the target sequence.

BRIEF DESCRIPTION OF THE DRAWINGS

FIG. 2A lists the partial sequence of the double stranded DNA (SEQ ID 1) used in the construction of the vector of the present invention (pANTI-T and M13-pANTI-T);

FIG. 2B lists the sequence (SEQ ID 2) which includes the inverted tandem repeats and restriction endonuclease sites that form, after insertion of the target sequence(s) and subsequent single stranded conversion, the stem of the stem-loop cloning vector; and FIG. 2C represents the dsDNA after insertion of the target sequence.

| Lane No. | |
|---|---|
| 1 | 1 Kb ladder |
| 2 | Isolate 1 (pANTI-T with 660 bp target insert) |
| 3 | Isolate 1 digested with Hind III |
| 4 | Isolate 1 digested with EcoR1 (not included in stem but included outside the inverted repeats) |
| 5 | Isolate 1 digested with Not 1 |
| 6 | Isolate 1 digested with S1 nuclease. |

The high molecular weight bands on the gel represent forms of helper phage used in single stranded rescue.

Figure 6:
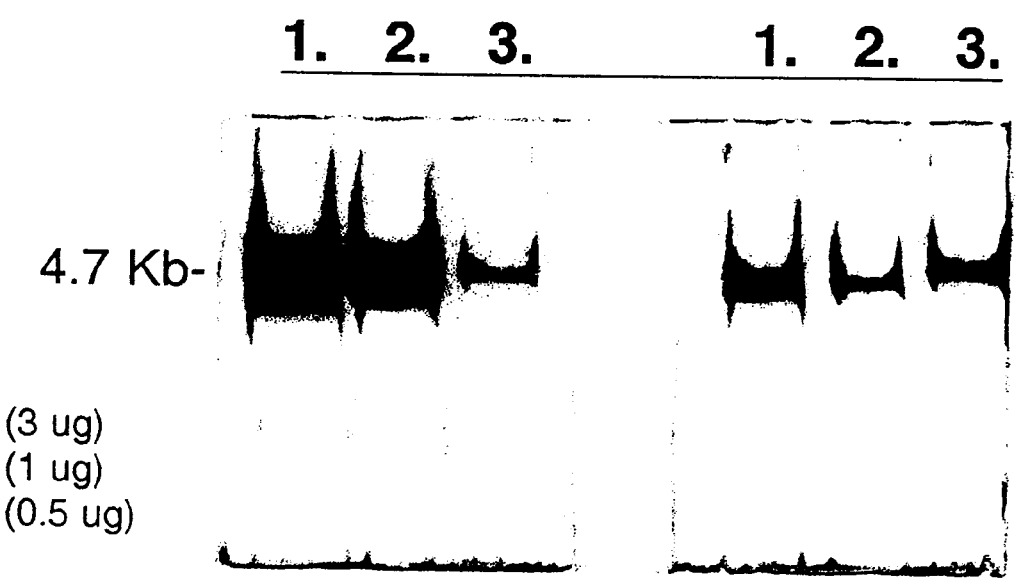

FIG. 6 is a Northern blot probed with the PANTI-T generated antisense ssDNA transferrin receptor probe (first exposure time with standard random labelling of cDNA probe (second three lanes) using the random labelling protocol of Maniatis, et al. (see infra).

| Lane No. | |
|---|---|
| 1 | human liver mRNA (3 $\mu$g) |
| 2 | Human liver mRNA (1 $\mu$g) |
| 3 | human liver mRNA (0.5 $\mu$g). |

DETAILED DESCRIPTION OF THE INVENTION

The cloning vector and method of the present invention takes advantage of genetic elements found in the normal life cycles of many prokaryotic and eukaryotic viruses, and those skilled in the art will recognize that functionally equivalent elements can be fulfilled by unrelated viral forms. Combined with those elements is a perfect inverted tandem repeat in which the bases making up the repeat structure additionally code for restriction endonuclease sites and/or other functional genetic elements. With this combination, the cloning vector of the present invention provides prokaryotic or eukaryotic mediated plasmid vectors capable of producing single stranded DNA during the intra-cellular life cycle. In the case of the filamentous bacteriophages (e.g., F1, Fd M13, etc.), this single stranded DNA intermediate is directed by the intergenic (IG) region. In the case of retroviral mediated single stranded DNA (ssDNA) conversion intermediates, virtually the entire viral genome (but most certainly the tat, psi, LTR's and pol functions) is advantageously employed to obtain the RNA to ssDNA conversion intermediate.

Such vectors advantageously include five elements:

1. A site or sites that clones in DNA target fragments of interest in between the inverted tandem repeat(s) (see below) which serve as the "stem" forming units (restriction endonuclease type I, II, IIs, or type III sites; blunt end ligation sites or T-overhang PCR cloning sites serve this function). Alternatively, target sequences of interest are synthesized "in toto" [an application that may be more appropriate if the target sequences are to serve as antisense or triplex forming oligos (triplex forming oligonucleotides) and ligated directly into the functional vector in between the inverted tandem repeat(s) which serve as the "stem" forming units (see below).

2. Single stranded rescue of the vector and insert through filamentous phage DNA replication control elements (e.g., "IG" region) or a vector constructed from a filamentous phage such that rescue is not needed. For instance, any F1/M13/Fd phage derivative elements which signal single stranded DNA replication (intergenic or "IG" region) of one of the plasmid's DNA strands serve this function. Single stranded DNA (ssDNA) intermediates from retroviral genomes (i.e., the intermediate from RNA to ssDNA) also serve this function if the plasmid or episome is designed for single stranded DNA conversion in eukaryotic cells.

3. An inverted tandem repeat which flanks both sides of the cloning site (whether cloned sequences of interest or with synthesized sequences of interest) and which forms a stable secondary "stem-loop" structure while in the single stranded DNA intermediate form (this formation may occur either in vivo or in vitro). This element is constructed using any combination of DNA base pairs as long as the sequence forms an inverted tandem repeat and the inverted tandem repeat is capable of forming a stem-loop structure with the loop comprising the cloned in sequence of interest.

4. The fourth element involves inclusion in the inverted tandem repeats of the functional genetic element(s) of interest. A number of such elements are utilized to advantage. One option is to include any restriction endonuclease (type I, II, IIs or III) sites desired in the inverted tandem repeat(s) such that the formation of the "stem" of the "stem-loop" structure (from the single stranded intermediate) also forms a new single or multiple restriction endonuclease site(s) capable of being cleaved (i.e. because the "stem" of the "stem-loop" structure is now double stranded). Another option is to design the inverted repeats to contain eukaryotic or prokaryotic and/or prokaryotic receptor recognition sites, promter, or promoter/enhancer elements to drive the expression of the target sequences in isolated cis-oriented fashion. Combinations of restriction sites or other functional genetic elements may be included in the inverted tandem repeats depending on the base pair composition chosen for the construction of inverted repeats.

It is generally preferred to use synthetically constructed functional genetic elements in the inverted tandem repeats since it is unlikely that a naturally occurring inverted repeat would have the properly aligned restriction sites.

5. The vector also includes a fully functional replicon so that replication of the construct of the present invention occurs in a permissive host organism. Both prokaryotic and eukaryotic replicons will function in this capacity (depending on the cell type in which the vector is designed to carry out its functions).

Although the cloning vector of the present invention preferably includes the elements listed above, multiple slightly variable forms can also be constructed to yield a vector that produces insert specific sense or antisense [depending on the direction the insert (or "target" sequence) is cloned in relative to the orientation of the vector itself] with these elements.

Figure 1:
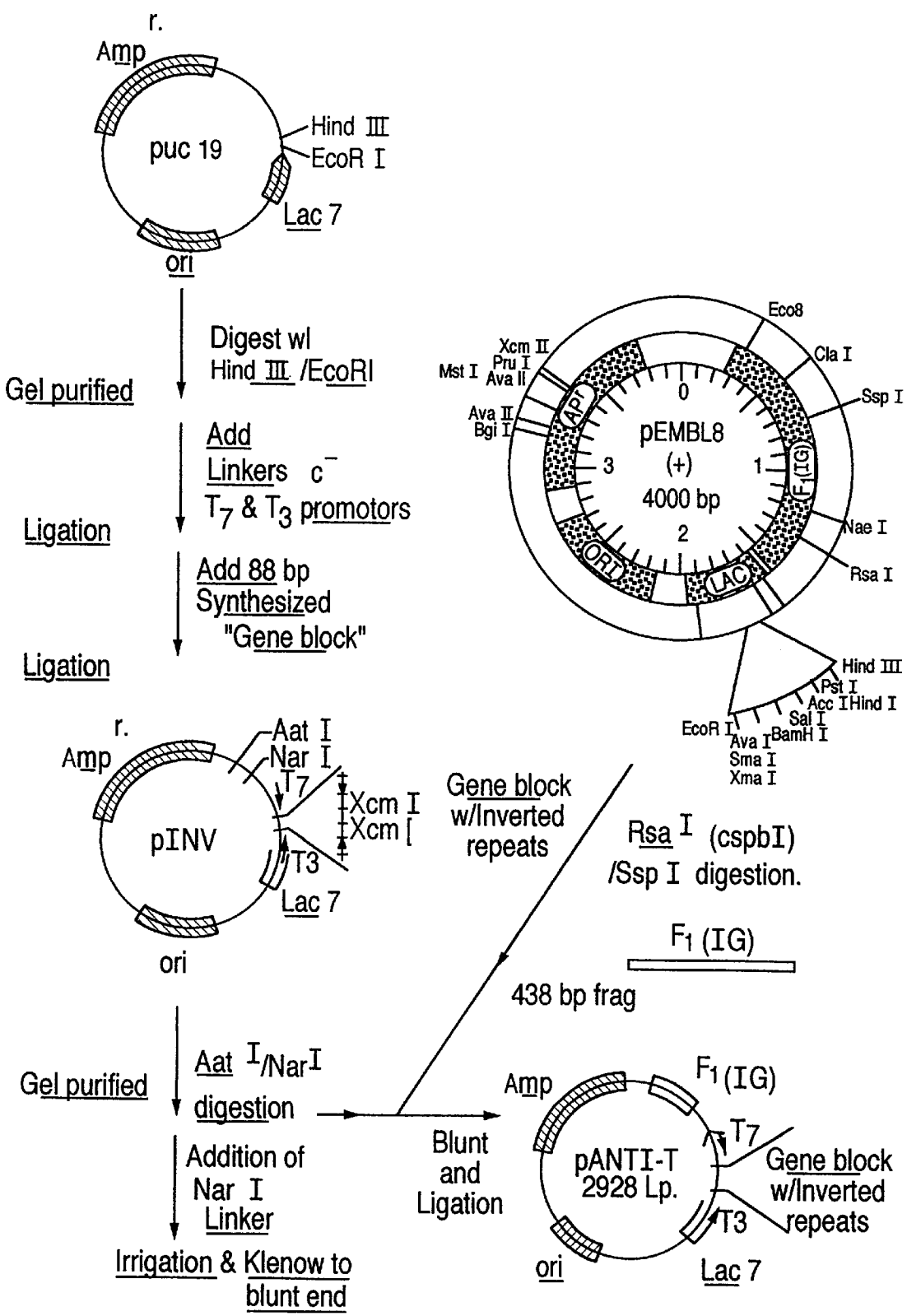
FIG. 1 is a schematic representation of the steps involved in producing a presently preferred embodiment of the cloning vector of the instant invention.

The process of making a cloning vector in accordance with the present invention begins by combining in a functional chimera the five elements listed previously with a user identified target nucleic acid sequence of interest. This target sequence is, for instance, a prokaryotic or eukaryotic gene sequence, genetic control element(s), antisense sequence(s), or potential triplex sequence(s). Next, the particular target sequence(s) is ligated into a previously designed cloning vector which has been constructed to contain these aforementioned five elements outlined above as shown in FIG. 1 (as an example). Following transformation or transduction of the constructed chimera into appropriate permissive hosts with any needed helper functions or positive selection criteron necessary for that particular construct (e.g., helper phage functions in the case of F1, Fd, M13, or Pol, Gag and Env products in the case of retroviral vectors), the production in vivo (or in vitro)) of single stranded DNA is completed. After single stranded DNA conversion is completed, the tandem inverted repeats (now with ligated target sequence(s) placed in between) will favor formation of the so-called "stem-loop" structure shown in FIG. 4. This structure places the functional genetic elements or recognition sequence(s) (which are contained in the sequence make-up of the inverted tandem repeats) in a cis-oriented fashion (i.e., the "stem") to act upon the target sequence(s) (i.e., the "loop") and perform directed functions to these target sequence(s) in vivo or in vitro.

The present invention can be better understood by reference to the following specific embodiments thereof, it being recognized by those skilled in the art that the embodiments described are set out by way of illustration and that the invention is not limited to only these specific embodiment. In the first example, the phagmid designated "pANTI-T" was produced for use in expressing the target sequence in *E. coli*. The second example illustrates production of a vector which is derived from a filamentous phage and which is designed for ssDNA conversion in prokaryotic cells without the need for helper phage functions.

Reagents were obtained from Boehringer Mannheim, U.S. Biochemical Corp. (Cleveland, Ohio) (USB), Sigma Chemicals and as gifts from Dr. Mark Emmett (University of Texas, Houston). Oligonucleotide synthesis products were obtained through Genosys, Midland Reagent Co. or as generous gifts from S. Tylor. The *E. coli* strain used through experimental protocols was JM-109 (recA1, endA1, gyrA96, thi, hsd1kZ, supE44, relAI, Δ(lac-proλB), [F', traD36, proAB, lacZΔM15]. Helper phage used was R408, VCS-M13. Long term storage of developed transformed strains with constructed vector was accomplished by mixing 1 ml. of stationary culture with 1 ml. sterile glycerol and storing at −70° C. Bacterial strains were grown in either 2YT or I.B supplemented with 50 μ/ml Ampicillin if transformed with vector constructions. All transformations, restriction endonuclease digestions, and ligations were carried out according to standard procedures recommended by J. Seabrook, E. F. Fritsch, and T. Maniatis, "Molecular Cloning: A Laboratory Manual," 2d Ed., Cold Spring Harbor Press (1989), hereinafter referred to as "Maniatis, et al." and incorporated herein in its entirety by this specific reference thereto. Competent cells were produced by standard calcium shock procedure also as per Maniatis, et al.

As a first step in producing the pANTI-T phagmid, the plasmid pUC19 (see FIG. 1) was digested with Hind III and EcoR1 (sites which are contained in the poly linker region of the alpha-complimenting portion of lacZ) and purified by gel electrophoresis (0.8% agarose in Tris acetate EDTA (TAE) at 45 V×1 hr.; the band was then cut out and electroeluted). Those skilled in the art will recognize from the above disclosure that the pUC19 plasmid was selected as the starting material because it includes one (a replicon) of the elements set out above as desirable elements comprising the construct of the present invention, but that it is possible to start with many other plasmids and add each element in serial fashion. This plasmid was also selected partly as a matter of convenience because of the presence of lacZ and ampicillin resistance gene, both of which facilitate screening of colonies by their blue or white color and resistance to ampicillin agar plates as set out below. Next, two non-phosphorylated linkers (having compatible ends to Hind III and EcoR1, though designed to destroy the reformed Hind III and EcoR1 restriction sites in the gene block described below) which contain the promoters for T7 and T3 (the latter being described in detail in U.S. Pat. No. 5,017,488) were ligated to the purified plasmid fragment under standard conditions at 12° C. overnight. To this was added (again referring to FIG. 1) a 88 bp synthesized gene block (double stranded and phosphorylated) which contained complimentary cohesive ends to the previously ligated EcoRI and Hind III linkers. This gene block (SEQ ID 1) was synthesized to contain elements (1), (3), and (4) set out above, element (3) being in the form of a perfect inverted tandem repeat of 17 base pairs which included, within the repeats, two restriction endonuclease enzyme recognition sequences for Hind III and Not I (element(4)). Additionally, other restriction sites were included in this gene block which were located outside of the inverted repeats. The sequence of this 88 bp gene block is set out in FIG. 2A and (SEQ ID 1). This was then allowed to anneal with the previously linker ligated plasmid at 75° C. for 15 min. and cooled slowly to room temperature. This mixture was then again ligated under standard conditions overnight.

Isolation of this plasmid, termed pINV (FIG. 1), was obtained after transformation (e.g., reproduction in progeny cells) was performed and blue colonies were picked (with the addition of 25 μl of a 40 μg/ml Xgal (Sigma) solution (which turns blue when metabolized by the lacZ gene) and 100 μl of a 40 mmol IPTG solution spread on the surface of the plates), the blue colonies indicating these cells in which the reading frame was preserved. Plasmid isolation was performed by mini-alkaline lysis procedure according to Maniatis, et al. Isolated plasmid was then confirmed by comparison to the band corresponding to the expected molecular weight as determined by gel electrophoresis (0.8 agarose in TAE).

Figure 3A:
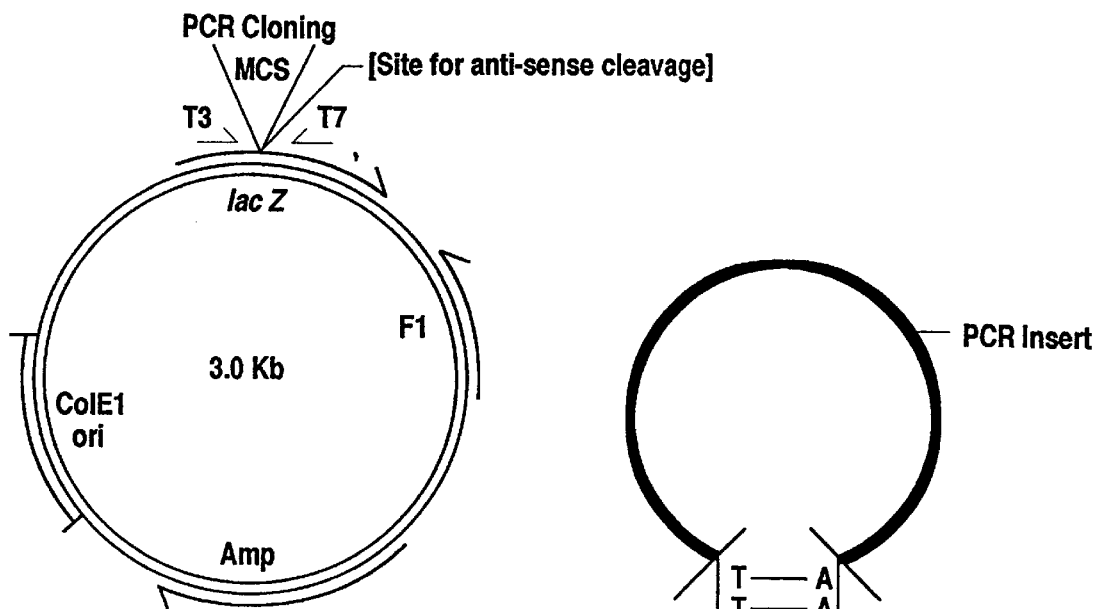
FIGS. 3A and 3B are schematic representations of the PANTI-T cloning vector (ATCC Accession No. 209678) produced by the method of FIG. 1 and including the sequence of FIG. 2A.
Figure 3B:
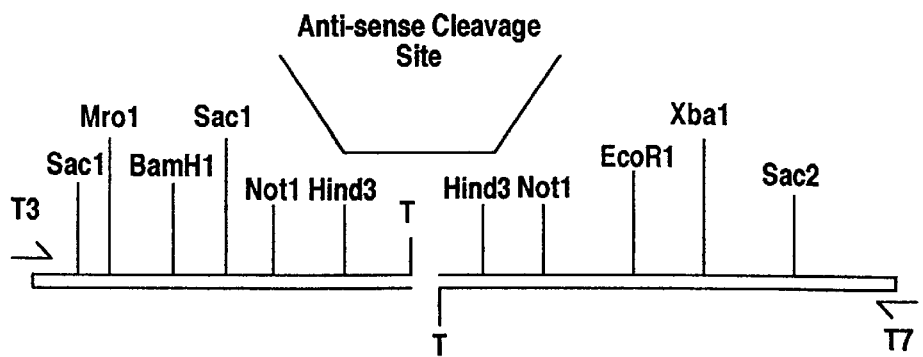

Element (2) listed above was then added to pINV as follows. The intergenic portion (e.g., the portion that signals single strand conversion) of F1 bacteriophage was obtained from the double stranded phagmid EMBL8 (FIG. 1) and a 438 bp fragment was obtained by digestion with Ssp 1 and Rsa 1 (Cspbl) and purified by gel electrophoresis. pINV was then digested with Aat II and Nar1 and again purified by gel electrophoresis. A spacing linker with compatible ends to Nar1 was ligated to the gel purified pINV fragment overnight. The ligated mixture was then blunt ended by the addition of Klenow fragment and allowed to proceed for 4 hrs. under standard conditions. Finally, 438 bp fragment which contains the F1(1G) portion was ligated to the blunt ended pINV vector overnight. Again, blue colonies were picked and screened for proper molecular weight recombinants. The resulting vector was termed pANTI-T, ATCC Accession No. 209678 (shown in more detail in FIGS. 3A and 3B).

A second embodiment of the vector of the present invention was made by incorporating the previously described 88 bp gene block which contained the synthetic polylinker/inverted repeat elements into an M13 cloning vector called M13mp8. Specifically, double-stranded RF form of M13mp8 was digested in the polylinker with EcoRI and Hind III and purified by gel electrophoresis and subsequent electoelution. The 88 bp gene block (SEQ ID 1) was then prepared by cleavage with Sac II and BamHI synthetic linkers EcoRI/SacI1 and Hind III/BamHI were designed so that the reading frame of the lacZ gene would not be interrupted. The purified M13mp8 fragment, prepared polylinker and small connecting linkers were adjusted to approximately the same molar-ends concentration (100 pM) and allowed to anneal at 37° C. for 30 min. then ligated under standard conditions at 12° C. overnight. Transformation of this ligation mixture was again performed the next day with previously made competent cells (JM109) by the method previously outlined. The only difference with this construct is that phage plaques, not bacterial colonies are obtained. After heat shock and growth in L.B. for 1 hr (without antibiotics), 100 μl of this cell suspension was added to 7.5 ml of melted top agar at 55° C. and 50 μl of a 40 μg/ml X-gal (in dimethyl formamide) and 2 mM IPTG final concentration. The top agar was mixed briefly and plated on 2 day old L.B. plates with incubation at 37° C. overnight. The following morning, blue plaques were picked and isolated for analysis of appropriate construct. This new construct was named M13-ANTI-T.

The above-described pANTI-T vector was used for cloning in the following manner. Included within the above-described 88 bp gene block segment (inside of the flanking inverted repeats) were two restriction sites for Xcm1 which, when cut, produced thymine 3', thereby providing element (1) listed above in the form of T-overhangs. Although those skilled in the art will recognize that any restriction recognition site could have served for a cloning site between the inverted repeats), T-overhangs were included in the sequence for the purpose of facilitating PCR fragment cloning. pANTI-T was digested with XcmI (USB). 1 μg of pANTI-T phagmid vector was digested at 37° C. for 1 hr. at a volume of 20 μl with the addition of 3 units XcmI. Confirmation of complete digestion was made by running a 0.8 agarose gel and noting the change of migration pattern of nicked coiled and supercoiled forms to linear form migrating at approximately 3.0 kb. A 660 bp fragment test piece was generated by PCR amplification of cDNA derived from human liver (obtained using the techniques of cDNA synthesis set out in Maniatis, et al.). Confirmation of this amplified fragment was determined by 1.5% agarose gel electrophoresis. 2 μl of this amplified product (corresponding to approximately 25–50 ng of DNA) was added to 50 ng (1 μl) of the pANTI-T vector and ligated in a total volume of 10 μl with 1 μl of 10× buffer and 5 units of T4 ligase (Boehringer Mannheim) and incubated at 12° C. overnight.

Transformation was carried out by the following procedure. Competent cells were prepared by standard calcium shock procedures and frozen for later use. Frozen tubes were thawed on ice and, being very gentle with the cells (i.e., no vortexing or pipetting), thawed tubes were tapped to ensure that the cells were at the bottom of the tube and were adequately mixed. Next, 2 μl of 0.5 M 2-mercaptoethanol solution was added to 2 μl of the ligation mixture and incubated on ice for 30 minutes. Next the cells were heat shocked at 42° C. for exactly 60 seconds. The mixture was then placed back on ice for 1–2 minutes. Lastly, 400 μl of Luria Broth (L.B.) without antibiotics was added and incubated for approximately 1 hour with shaking at 37° C. This transformant mixture was then plated with 50 μl on 1–2 day old L.B. plates containing 50 μg/ml Ampicillin, 25 μl X-gal at 40 μg/ml (in dimethyl formamide), and 100 μl of 40 mM IPTG solution with a hockey stick and incubated overnight at 37° C.

When plated, blue/white colonies will appear because of the inclusion of the lacZ gene (white colonies), which disrupts the function of the lacZ gene, in the pUC19 plasmid from which pANTI-T was made or T:T mismatch which preserves the lacZ reading frame (blue colonies). The pANTI-T phagmid vector produces ssDNA of the target sequence(s) with minimal vector sequences (only a few bases), and produces antisense in a directional fashion. The stem-loop configuration enables the cloning vectors of the present invention to direct double-stranded intermediates in a cis-oriented fashion to produce the single-stranded target sequence (in this case, the 660 PCR fragment ligated into pANTI-T). As a result of the inclusion of the T7 and T3 promoters in the linkers used to destroy the reformed restriction sites described above, pANTI-T produces single-stranded antisense of a target sequence when a $T_3$ primed sequencing reaction of a cloned product yields the sense sequences of a PCR product or when a $T_7$ primed sequencing reaction of a cloned product yields the anti-sense sequences of the PCR product. Therefore, to isolate single-stranded antisense from the pANTI-T vector, clones which have the 5' → 3' sense strand on the same $T_3$ primer strand are isolated or, if using a $T_7$ primed sequencing reaction, those clones that have the anti-sense strand on the same $T_7$ primer strand are isolated.

After deciding on appropriate antisense isolates, the sequence was confirmed by sequencing reactions which were primed by $T_7$ and using the Sequenase sequencing system (USB) according to the supplier's recommendations. Early in the morning, 100 mls of L.B. 50 μg/ml Ampicillin was inoculated with an overnight culture of 10 mls of L.B., started from a colony obtained on minimal media plates (assuring selection for F') and grown with the addition of 50 μg/ml Ampicillin (maintains pANTI-T vector) at 37° C. in a shaking incubator, and grown at 37° C. to $OD_{600}$ of 0.3 with vigorous shaking. Helper Phage R408 at 0.0005 volume (50 μl of Helper Phage, which results in approx. 20:1 multiplicity of infection (MOI) was utilized and incubation continued for another 8 hours (some single stranded rescue procedures respond to different MOIs, and previous trials of 10:1, 1:1, and 1:10 MOI were also performed). The entire culture was then heated at 65° C. for 15–20 min. and clarified by centrifugation 17,000×g for 5 min. This supernatant was transferred to a fresh tube and 0.25 volume of 3.5 M ammonium acetate in 20% PEG solution, pH 7.5, was added, mixed well, and let to stand at room temperature for approx. 15–20 min. (this step precipitates the ssDNA phage). Tubes were then spun at 17,000×g for 10 min. to remove all supernatant (a white pellet was visible at this point which represented the single strand phagmid/insert/helper phage). Finally, the pellet was re-suspended in 0.10 (10 mls) original volume T.E. buffer (10 mM Tris-HCL, pH 8.0; 1 mM EDTA).

An equal volume phenol/chloroform solution (equal volumes of phenol and a 24:1 solution of chloroform and isoamyl alcohol) was added to disrupt the phage protein coat and the mixture was vortexed vigorously for 1–2 min. A spin and repeat extraction 2 times was performed until a minimal interface remained. The aqueous phase (upper phase) was then transferred to a new tube. The DNA was then precipitated by adding 0.1 vol. (of the aqueous phase volume) 3 M Na acetate, pH 5.2, and 2.5 volumes ice cold ethanol and incubated at 20° C. overnight. This mixture was then centrifuged at 17,000×g for 20 min. The pellet was then partially dried by inverting the tubes for approximately 10 min. (making sure all traces of ethanol were removed). This pellet was then resuspended in 250 μl of $H_2O$ and absorbance at O.D. 260 was read (extinction coefficient for ssDNA approximately 40 μg/ml per 1 O.D. unit).

Figure 4:
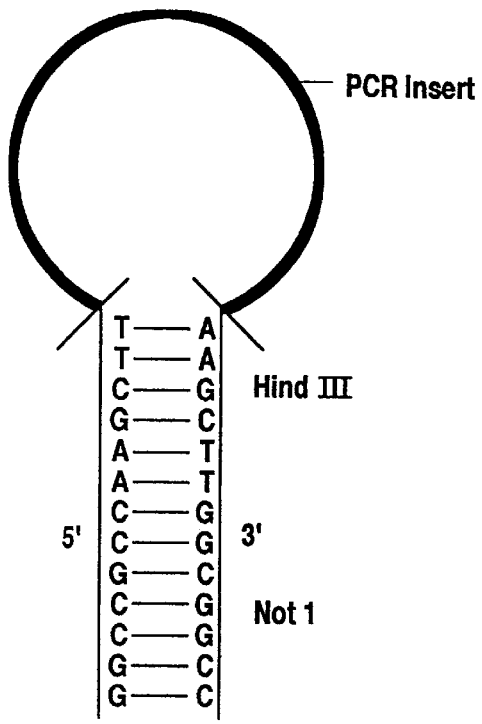
FIG. 4 is a schematic partial representation of the stem-loop structure which is obtained (or formed) after (ssDNA) conversion of pANTI-T single stranded DNA vector of FIG. 3 after ssDNA conversion or thermodynamically favored formation of the stem by base pairing of the tandem repeats included in the sequence of FIG. 2.

Antisense Rescue and Electrophoretic Data pANTI-T was designed so that after an insert of choice has been cloned in, a thermodynamically favorable stem-loop structure is formed after single-stranded DNA conversion by the presence of the perfect 17 base pair inverted repeat (SEQ ID 2). This stem-loop structure contains the target sequence(s) as the single-stranded "loop" and newly formed Not I and Hind III sites which are included in the double-stranded "stem" (FIG. 4). Digestion with Hind III will produce only 2 and 4 base (3'/5' overhangs respectively). Although Hind III is the site of choice for producing insert specific ssDNA, some inserts may disrupt the Hind III recognition site by interfering with the formed stem-loop secondary structure sufficiently to impede adequate endonuclease restriction digestion, however, Not I digestion is rarely affected by the type of insert.

Figure 5:
FIG. 5 shows the pattern of migration of the PANTI-T cloning vector produced by the method of FIG. 1 and having a 660 bp target sequence cloned therein on electrophoretic gel. Isolates were as set out in the following lanes and all isolates were converted to single stranded form such that apparent migration speed is approximately doubled.

To insure the presence of only the stem-loop structure of pANTI-T, 20 μl (corresponding to approximately 5 μg) of ssDNA phagmid was heated to 75° C. for 5 min. and allowed to cool slowly to room temperature (10 to 15 min). To verify the stem-loop structure, 4 μl of this sample was then digested with either Not I, Hind III, or EcoRI with 1 units of enzyme per 1 μg phage/insert brought up to a total volume of 20 μl and incubated at 37° C.×2 hrs. Additionally, 4 μl was also digested by S1 nuclease (which is specific for single-stranded DNA) only according to manufacturer's recommendations (2 μl of 10× buffer and 5 units S1 nuclease, brought up to 20 μl total volume with water). 10 μl of these digests, along with undigested ssDNA rescued material, was then analyzed on an appropriate 1.5% agarose gel in TAE at 55 volts for 1.5 hrs. The resulting gel is shown in FIG. 5, and as can be seen, the Hind III and Not I endonucleases, which can act only on dsDNA, were active whereas EcoRI was not, that site having been single stranded and not included within the stem. Likewise, S1 nuclease (active only on ssDNA) digested the entire phagmid/insert. Single stranded DNA migrates slightly more than twice as fast as double stranded marker. Thus as shown in FIG. 5, helper phage ran at about 6 Kb and the 660 base original PCR product ran at about 300 bp. The 660 base (lower) band showing in FIG. 5 was purified by microcentrifugation in Amicon spin filter tubes and end labelled with polynucleotide kinase and hybridized to the Northern blot by procedures described in Maniatis, et al. (lanes 1–3). The native transferrin receptor gene migrated at 4.7 Kb with this hybridization, demonstrating that the

---

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 67 base pairs
        (B) TYPE: nucleic acid
        (C) STRANDEDNESS: unknown
        (D) TOPOLOGY: linear (ii) MOLECULE TYPE: Other nucleic acid (xi) SEQUENCE DESCRIPTION: SEQ ID NO: 1:

CCGGATCCGA GCTCGCGGCC GCCAAGCTTA AGCTTGGCGG CCGCGAATTC    50

GCTCGAGCCG CGGGCTG    67

(2) INFORMATION FOR SEQ ID NO: 2:

(i) SEQUENCE CHARACTERISTICS:
        (A) LENGTH:  39 base pairs
        (B) TYPE: nucleic acid
        (C) STRANDEDNESS: unknown
        (D) TOPOLOGY: linear (ii) MOLECULE TYPE: Other nucleic acid (xi) SEQUENCE DESCRIPTION: SEQ ID NO: 2:

CTCGCGGCCG CCAAGCTTNN NAAGCTTGGC GGCCGCGAA    39

--- lower band from FIG. 5 was the 660 single stranded antisense target sequence. The same blot was stripped and was also probed with a random labelled double stranded pANTI-T vector which contained the 660 bp double stranded sequence with Klenow fragment (Maniatis, et al.) and re-probed (lanes 4–6), once again indicating that the band revealed was the target sequence of interest.

Although described in terms of these specific examples, as noted above, those skilled in the art will recognize from this disclosure that there are many changes which can be made to the manner in which the individual components or steps of the invention function to achieve their respective intended result(s). For instance, in the case of the p-ANTI-T vector described above, the inverted tandem reports include Hind III and EcoRI restriction sites, but other vectors made in accordance with the present invention may include other such restriction sites, each such vector having restriction sites, or other functional genetic elements such as promoter or promoter/enhancer elements, or combinations of such elements, which are chosen for the end purpose contemplated for that specific vector. Likewise, the M13-ANTI-T vector described above illustrates one manner in which the stem-loop vector of the present invention is made using a derivative of a filamentous phage, e.g., ssDNA, rather than with the double stranded DNA of, for instance, the pUC19 plasmid. It is also clear that there are no limitations on the size, nature, and/or origin of the target sequence(s) that are incorporated into the vector of the present invention. All such changes are intended to fall within the spirit and scope of the following claims.

What is claimed is:

1. A cloning vector comprising a first nucleic acid sequence, a second nucleic acid sequence which comprises a replicon, and a third nucleic acid sequence which comprises an inverted tandem repeat flanking said first sequence and a restriction endonuclease site, said inverted tandem repeat forming the double-stranded stem of a stable secondary stem-loop structure with said first sequence being located in the single-stranded loop portion thereof.

2. The vector of claim 1 wherein said restriction endonuclease site comprises either Hind III and Not I, Hind III, or Not I restriction sites.

3. The vector of claim 1 wherein said restriction endonuclease site is selected from the group consisting of a restriction endonuclease type I, endonuclease type II, endonuclease type IIs, or endonuclease type III sites, and combinations thereof.

4. The vector of claim 1 wherein said restriction endonuclease site comprising the inverted tandem repeat acts in cis-oriented fashion after formation of the stem-loop structure.

5. The vector of claim 1 additionally comprising a single stranded DNA replication control element.

6. The vector of claim 5 wherein said replication control element is selected from the group consisting of a phage derivative which signals DNA replication and a DNA element from a retroviral genome.

7. A method of presenting an isolated single stranded nucleic acid sequence for subsequent operation thereon by an enzyme that binds with a specific recognition sequence comprising the steps of:

cloning double stranded DNA having a sequence of interest included therein into a nucleic acid construct, the sequence of interest comprising an inverted tandem repeat;

converting the double stranded DNA including the sequence of interest into a single stranded sequence;

forming the single stranded sequence into a stem-loop structure by Watson-Crick base pairing of the nucleic acids comprising the inverted tandem repeat in the sequence of interest, the nucleic acids comprising the sequence of interest having been selected so that, once formed, the stem of the stem-loop structure includes a specific recognition sequence to which an enzyme binds; and directing the function of the enzyme which binds to the specific recognition sequence in the stem of the stem-loop structure towards the sequence in the loop thereof.

8. The method of claim 7 wherein the stem-loop structure is formed after cloning the double stranded DNA having the sequence of interest therein into the nucleic acid construct.

9. The vector pANTI-T.

10. A bacterial cell having the vector of claim 9 transformed therein.

11. The vector M13-pANTI-T.

12. A bacterial cell having the vector of claim 11 transformed therein.

13. A stem-loop cloning vector formed from a double-stranded nucleic acid sequence by single stranded conversion comprising a tandem inverted repeat separated by a cloning site for insertion of a target nucleic acid sequence, said tandem inverted repeat forming the stem of the stem-loop cloning vector and the target nucleic acid sequence forming the loop of the stem-loop cloning vector.

14. The stem-loop cloning vector of claim 13 wherein the nucleic acids comprising said tandem inverted repeat are selected so as to form a restriction endonuclease site upon formation of the stem of the stem-loop cloning vector.

15. The stem-loop cloning vector of claim 14 wherein the restriction endonuclease site comprises either a Not I or a Hind III restriction site.

16. A bacterial cell having the cloning vector of claim 13 transformed therein.

17. A kit for producing single stranded DNA probes comprising the cloning vector of claim 13, instructions for the use of the cloning vector, and a container for holding the cloning vector and said instructions.

18. The kit of claim 17 wherein the nucleic acids comprising said tandem inverted repeat form a restriction endonuclease site upon formation of the stem of the stem-loop cloning vector.

* * * * *